United States Patent [19]

Tobin

[11] Patent Number: 5,662,598

[45] Date of Patent: Sep. 2, 1997

[54] SILICONE OCCLUSIVE DRESSING FOR PENETRATING THORACIC TRAUMA

[76] Inventor: Joshua M. Tobin, 2400 E. Cary St., Apt. No. 309, Richmond, Va. 23223

[21] Appl. No.: 671,404

[22] Filed: Jun. 27, 1996

[51] Int. Cl.$^6$ .................................................. A61F 13/00
[52] U.S. Cl. ................... 602/41; 602/53; 602/54; 602/58; 604/307
[58] Field of Search .................... 604/304, 307; 602/41, 42, 43, 53-58

[56] References Cited

U.S. PATENT DOCUMENTS

| Re. 33,353 | 9/1990 | Heinecke | 428/40 |
|---|---|---|---|
| 4,413,621 | 11/1983 | McCracken et al. | 128/156 |
| 4,465,062 | 8/1984 | Versaggi et al. | 128/1 R |
| 4,717,382 | 1/1988 | Clemens et al. | 604/122 |
| 5,090,406 | 2/1992 | Gilman | 602/47 |
| 5,160,322 | 11/1992 | Scheremet et al. | 604/122 |
| 5,195,977 | 3/1993 | Pollitt | 604/122 |
| 5,232,702 | 8/1993 | Pfister et al. | 424/448 |
| 5,250,043 | 10/1993 | Castellana et al. | 604/336 |
| 5,263,922 | 11/1993 | Sova et al. | 602/59 |
| 5,478,333 | 12/1995 | Asherman | 604/304 |

*Primary Examiner*—Robert A. Clarke
*Attorney, Agent, or Firm*—Donal B. Tobin

[57] ABSTRACT

An occlusive wound dressing for penetrating thoracic trauma including a silicone impregnated gauze pad covered by an overlapping thin, flexible, plastic sheet having adhesive about the perimeter of three sides of said gauze pad and having an unadhered marginal area on the fourth side of said gauze pad to allow said wound dressing to be applied to the wound so that the unadhered marginal area of the outer sheet provides a flutter valve to permit the flow of undesired fluids such as air and blood out of the wound, for example, during expiration but preventing the in-flow of fluids into the wound during inspiration.

17 Claims, 3 Drawing Sheets

5,662,598

SILICONE OCCLUSIVE DRESSING FOR PENETRATING THORACIC TRAUMA

BACKGROUND OF THE INVENTION

The present invention relates to a bandage that may be applied directly to the patient's skin and more particularly to a silicone impregnated occlusive dressing for a penetrating thoracic wound.

The process of breathing depends on maintaining a proper pressure differential between the pleural cavity and the outside environment. Normally, visceral and parietal pleura are separated by the pleural space which is filled with pleural fluid. When one's diaphragm and intercostal muscles contract during inspiration, the rib cage expands, pulling the pleural pleura away from the visceral pleura. A negative pressure in the pleural space ensures that the visceral pleura follows the pleural pleura as it expands outwardly. A net negative pressure is then developed within the lungs themselves, and positive atmospheric pressure forces air into the lungs. This is the phenomenon know as inspiration.

In penetrating thoracic trauma, an object like a bullet, knife or metal fragment penetrates the chest wall or both the chest wall and the lung itself and exposes the pleural space to the atmospheric pressure of the outside environment. When the normal negative pressure of the pleural space is exposed to the more positive atmospheric pressure, outside air flows into the pleural space through the wound or through the punctured lung causing an open pneumothorax to develop. The net negative pressure within the plural space diminishes. The visceral and parietal pleura separate as the outside air compresses the lung and forces the lung and chest wall farther apart. As air and other fluids like blood released by vessels damaged in the trauma continue to enter the pleural space, ventilation of the affected, and now compressed, lung becomes increasingly difficult. The pressure needed to inflate the lung via normal physiological mechanisms is no longer attainable. As even more fluid continues to enter the pleural space through the open wound, the heart, the great vessels of the heart and the opposite lung become compressed under the increasingly positive pressure in the thorax. The opposite lung eventually collapses, and blood flow to and from the heart decreases. Cardiac output falls significantly, cardio-pulmonary collapse and unconsciousness occur, followed soon thereafter by cardio-pulmonary arrest and death.

It is, therefore, important that the wound dressing applied in the field seals the chest wall to prevent air from entering the pleural space through the wound. At the same time the dressing must allow air entering the pleural space through a punctured lung and blood that may have leaked into the pleural space as a result of the trauma, be allowed to evacuate from the wound. Such a dressing allows the patient to at least partially reestablish the proper pressure differential in the pleural cavity. With the proper dressing applied quickly in the field, the patient's natural reflex to continue to attempt to breathe can be accommodated and even facilitated. A dressing designed to treat a penetrating thoracic chest wound must be able to seal the wound at sometimes and, equally importantly, allow it to open at others.

There is particularly a need for an improved field dressing for penetrating thoracic wounds to be used by emergency medical personnel at the scene of an injury. Penetrating thoracic trauma is unique because wounds which compromise the chest wall are often rapidly fatal. As explained above, if a bullet, knife or other high force projectile, like metal fragments from a motor vehicle accident, punctures the chest wall, then the normal mechanism by which the lungs operate is affected, with life threatening consequences.

The current occlusive dressings used to treat penetrating thoracic trauma in the field is a gauze pad impregnated with petroleum jelly. The occlusive gauze prevents further entry of air into the pleural space, and thereby prevents further damage resulting from positive intrapleural pressure. In the event that the lung itself has been punctured in the injury, an increase in intrapleural pressure may occur in spite of, and perhaps even because of, a properly applied occlusive dressing with an adequate seal. The resulting tension pneumothorax is often rapidly fatal. To correct for this possibility, it is advisable that the occlusive gauze dressing be taped to the skin on only three sides of the usually square gauze pad, thereby allowing air from a pleural space to escape via the untaped fourth side of the dressing. The often stressful environment surrounding patients afflicted with penetrating thoracic trauma and the "load-and-go" speed with which emergency service personnel must work, can make it difficult to properly apply such a wound dressing. The result can be either an inadequate seal which allows further development of an open pneumothorax, or a totally occlusive dressing, which does not allow for the passive relief of a tension pneumothorax.

The use of petroleum as the occlusive medium for the dressing can also be a problem. One of the first treatment modalities for penetrating thoracic trauma is the administration of oxygen. The application of petroleum products to a wound from which 100% oxygen may be flowing, in the oxygen rich environment found in the patient compartment of an ambulance, introduces the risk of fire. Petroleum products can also cause death to lung tissue upon contact. In the event that a petroleum product does contact the lung through the open chest wound, the possibility of tissue necrosis is significant.

Also, petroleum occlusive dressings that are adapted for this purpose in the field are removed from sterile packaging and applied to the open wound with non-sterile hands. The risk of infection can be high. Also, the size of the petroleum occlusive dressings used currently is adequate to cover small or single entrance wounds like bullet wounds and puncture type stab wounds. It is, however, too small to adequately treat larger wounds like deep slashing stab wounds, shotgun blasts and injuries due to metal motor vehicle fragments.

There is a need for a compact specially designed wound dressing for penetrating thoracic trauma which is sterilely packaged and can be quickly and easily applied to the wound in the field with a minimum risk of contaminating the dressing. The dressing should also be large enough to cover the variety of types of wounds that are found in the field. It is also important to eliminate the petroleum jelly and to use an occlusive medium which is more compatible with the other therapies that need to be applied to a patient suffering from a penetrating thoracic trauma.

SUMMARY OF THE INVENTION

The present invention provides an integral, compact occlusive wound dressing that can be easily used and applied in the field for a large variety of wounds and can be used consistent with oxygen therapy and the other modalities of therapy used in the field. The wound dressing includes a gauze pad having a perimeter defining an area sufficient to occlude the wound. The pad is impregnated with silicone jelly. A thin flexible outer sheet overlaps the silicone impregnated pad on all four sides. The outer sheet has an adhesive area coveting at least a major portion of the sheet and overlaying the pad and also includes a marginal area extending along one side of the sheet. The border between the marginal area and the remainder of the sheet defines an interior side of the marginal area and is aligned co-linearly with an adjacent portion of the pad perimeter. An adhesive layer secures the sheet adhesive area to the top of the pad and overlaps three sides of the pad so that the dressing may be adhesively affixed to the patient about the wound but will leave the dressing unadhered to the skin on the remaining side of the pad so that undesired fluid can escape from the wound and drain out of the bandage.

The bandage is usually square or rectangular, but can be any convenient shape. The marginal area is usually a strip along one side of the sheet coveting the pad, but a large variety of geometrical arrangements between the sheet and the pad could be used. For example, one could have an oval pad centered on an oval outer sheet and the marginal area could be one or more radial passages running from the edge of the pad to the edge of the sheet. On the other hand, the pad could be offset from the center of the sheet so that the pad could be more closely positioned to the edge of the sheet and the marginal area would be disposed in that vicinity.

The adhesive layer between the pad and the sheet could be continuous or intermittent.

Release paper covers the entire adhesive area and marginal area of the sheet and encloses the pad between the release paper and the outer sheet. The entire assembly can then be packaged in a sterile package ready for use in the field.

BRIEF DESCRIPTION OF THE DRAWINGS

These and other features and advantages of the present invention will become apparent from the following detailed description of the preferred embodiment taken in conjunction with the following drawings.

DETAILED DESCRIPTION OF THE PREFERRED EMBODIMENT

Figure 1:
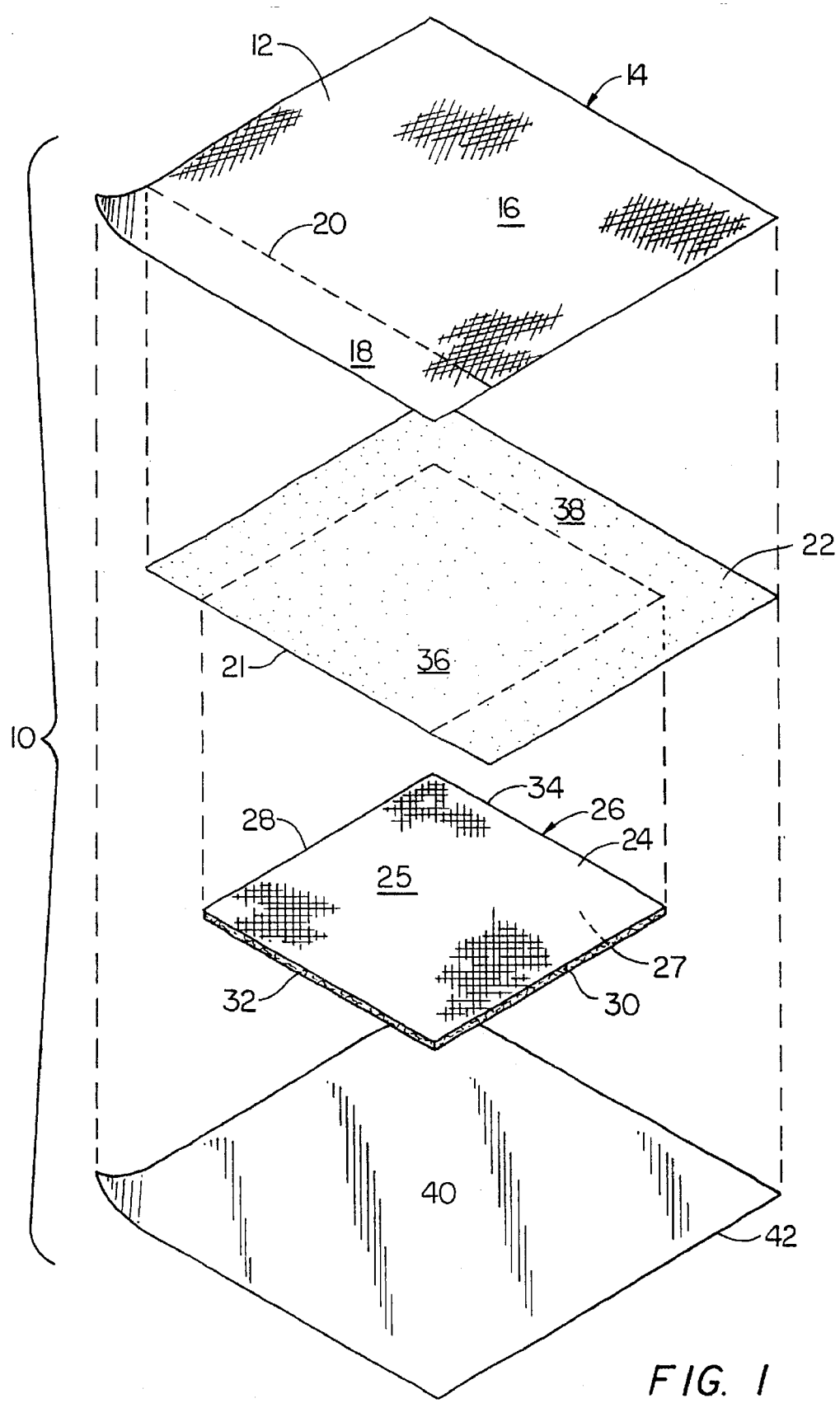
FIG. 1 is an exploded perspective of the various elements of the wound dressing of the present invention.

Referring now to FIG. 1, there is shown an exploded perspective of the elements of the wound dressing of the present invention generally designated as 10. Outer sheet 12 is made of a thin, flexible, material similar to that used on many bandages. It is preferably made of plastic and also preferably fluid impermeable. Outer sheet 12 has a perimeter 14 defining an area large enough to generously cover a variety of penetrating thoracic wounds. Outer sheet 12 includes two specific areas: the first being an adhesive area 16; and, the second being a marginal area 18 divided from adhesive area 16 by a border line 20 which is interior to perimeter 14.

Adhesive layer 22 covers adhesive area 16 of outer sheet 12. Adhesive layer 22 may be a continuous layer of adhesive or may be intermittent patterns of adhesive. I prefer a non-air permeable hypo-allergenic adhesive like, for example, adhesive No. 1524 sold by 3M Company and described, for example, in U.S. Pat. No. 5,478,333 at page 8, line 17.

A sterile cotton gauze pad 24 has a generally square shape with perimeter 26 and has top 25, bottom 27, left and right sides 28 and 30 and front and rear sides 32 and 34. Gauze pad 24 is aligned with respect to adhesive layer 22 such that adhesive layer 22 overlaps sides 28, 30 and 34 of gauze pad 26. The perimeter 21 of adhesive layer 22 is co-linearly aligned with edge 32 of gauze pad 36. By the same token, edge 32 of gauze pad 26 is aligned with border line 20 of outer sheet 12. It is clear from the drawings that marginal area 18 does not contain adhesive. Adhesive layer 22 has areas 36 which completely overlays top 25 of gauze pad 26 and area 38 outside the dotted line on adhesive layer 22 in FIG. 1 which overlaps gauze pad 26 and is available to adhere to the patient's skin during use.

Gauze pad 26 is impregnated with silicone jelly, for instance the well known KY brand jelly, sold by Johnson & Johnson of New Brunswick, N.J.

Release paper 40 is the same size as outer sheet 12 and has a perimeter 42 which is substantially co-linear with the perimeter 14 of outer sheet 12. Release paper 40 adheres to skin adhesive area 38 of adhesive layer 22 and overlays marginal area 18 of outer sheet 12. Silicone impregnated gauze pad 24 is, thus, encased within the envelope formed by outer sheet 12 and release paper 40. Release paper 40 is made of a standard material commonly used in disposable bandages.

Figure 2:
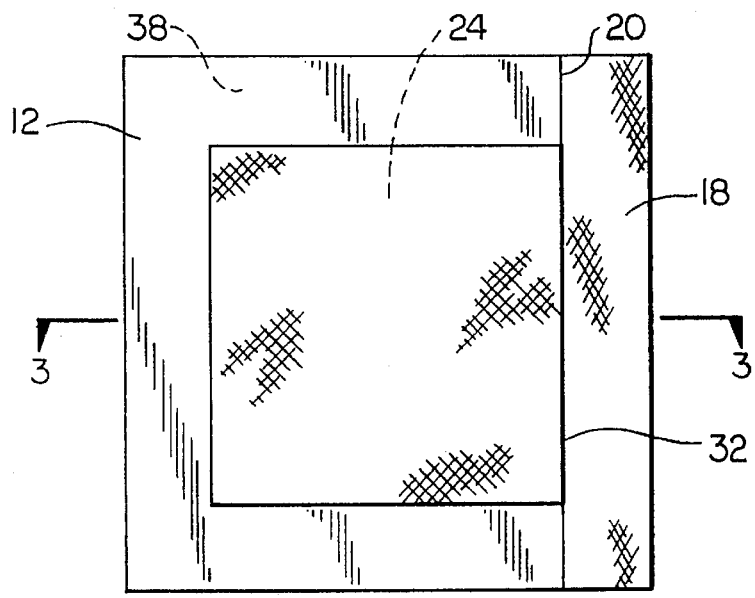
FIG. 2 shows a plan view of the dressing.
Figure 3:
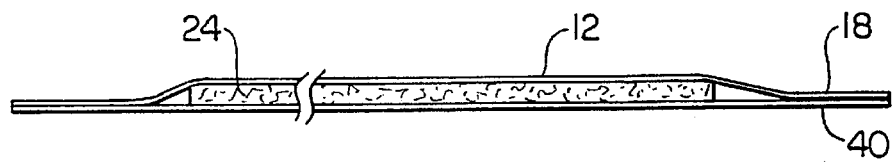
FIG. 3 shows an enlarged cross-sectional view of the dressing of FIG. 2 taken along lines 3—3 in FIG. 2.

In FIG. 2, there is shown a top plan view of the dressing shown in FIG. 1. The alignment of gauze pad 24 with the marginal area 18 so that edge 32 of gauze pad 24 is co-linearly aligned with border line 20 of marginal area 18 is clearly shown. FIG. 3 shows a cross-section taken along lines 3—3 in FIG. 2 and shows gauze pad 24 enclosed within the envelope formed by outer sheet 12 and release paper 40.

Figure 6:
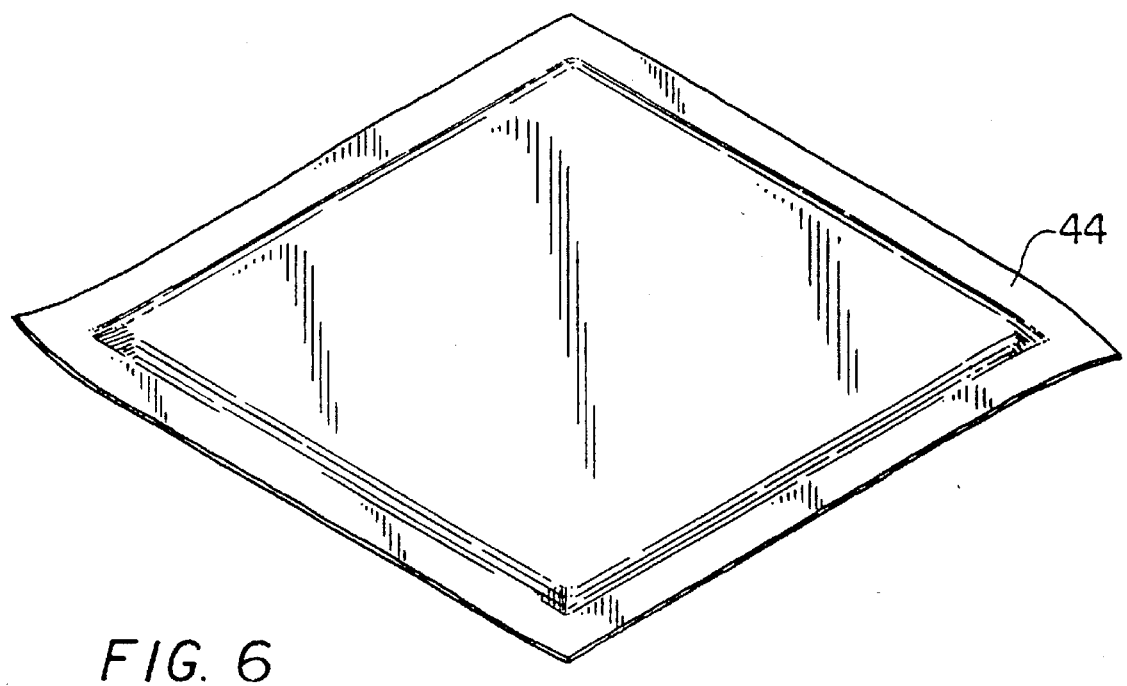
FIG. 6 shows the entire dressing in a surrounding package.

FIG. 6 shows the entire assembly of FIG. 1 further enclosed within a package 44 preferably a paper package of a kind commonly used on disposable bandages and which is applied under sterile conditions.

Gauze pad 24 preferably measures six inches by six inches to be large enough to generously cover a large variety of wounds. The adhesive layer is large enough to leave at least a one inch adhesive area for the skin on three sides of gauze pad 26. Outer sheet 12 is sized to completely cover the skin adhesive area 38 and also to provide a marginal area 18.

The use of dressing 10 is explained in connection with FIGS. 4 and 5. Bandage 10 is removed from its paper package 44. To open dressing 10 for use, one holds dressing 10 by the non-adhesive marginal area 18 in one hand and tears release paper 40 away with the other hand. Prior to application, the tissue in the area of the wound may be briefly cleansed of blood, sweat and other debris. The area may then be swabbed with an iodine solution. Gauze pad 24, which as explained above, is impregnated with silicone in such a way as to sterilize the gauze, is applied to a somewhat cleaner wound site. The brief preparation of the wound site serves two purposes, 1) to maintain as sterile art, environment as possible, thereby reducing risk of later infection, and 2) to ensure the most effective interface between the wound side and the adhesive side of the dressing thereby ensuring the best possible occlusive dressing.

Figure 4:
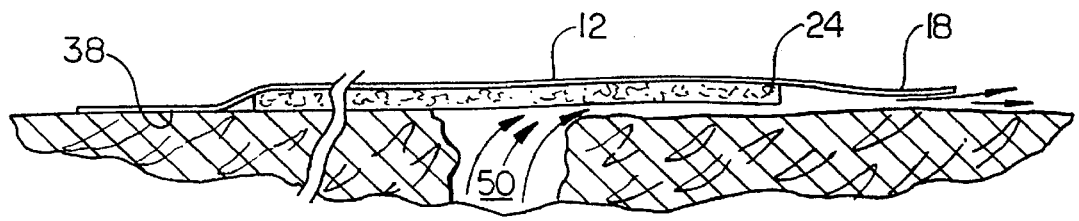
FIG. 4 shows the wound dressing applied to a wound and shows material passing from the wound between the pad and the patient's skin and out through the marginal area of the outer sheet which overlies the pad.
Figure 5:
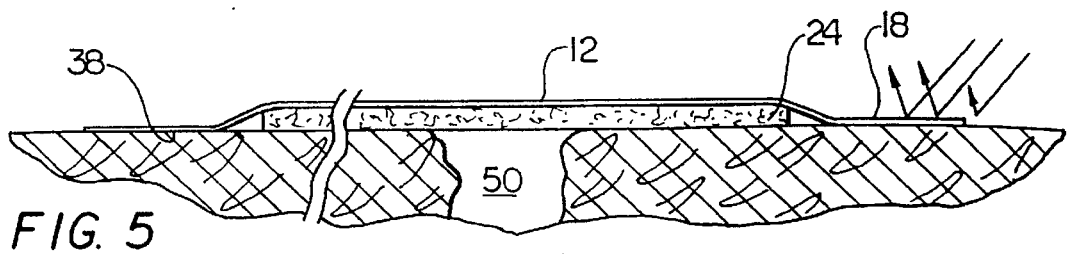
FIG. 5 shows the dressing on a wound with the pad and marginal area tightly sealing the wound against the ingress of the atmospheric air.

One can see from FIG. 4 that as air or other fluids exit the wound 50, as illustrated by the arrows in FIG. 4, usually during expiration, they enter the area under dressing 10. A positive pressure, relative to the outside, builds up under dressing 10 and these fluids are forced to the outside as the non-adhesive marginal area 18 separates from the wound site and allows the escape of fluid. When a negative pressure, relative to the outside builds up in the area under the dressing, usually during inspiration, air attempt to enter the wound. Non-adhesive marginal area 18 of the dressing now collapses against the wound site and prevents the entrance of such air as shown by arrows in FIG. 5. Thus, marginal area 18 acts as a flutter valve providing for the one-way flow of air and fluid out of the wound but prohibiting the flow of air into the wound.

Figure 7:
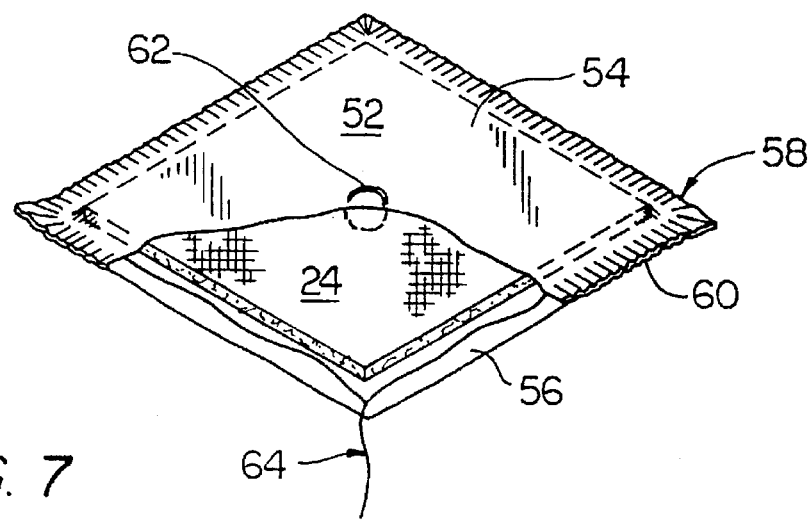
FIG. 7 shows an alternative embodiment of the gauze pad portion of the dressing shown in FIG. 1 wherein gauze pad portion is enclosed in an aluminum foil envelope.

FIG. 7 shows an alternative embodiment of the gauze pad 24 portion of dressing 10 shown in FIG. 1. In FIG. 7, gauze pad 24 is enclosed in an aluminum foil envelope 52 which has an upper sheet 54 and a lower sheet 56 crimped together around the perimeter 58 by means of a crimp 60. Upper sheet 54 may be connected directly to gauze pad 24 by means of a stitch or staple 62. Adhesive may also be used to attach upper aluminum sheet 54 to the confronting surface of gauze pad 24. The aluminum foil envelope of FIG. 7 can be substituted into FIG. 1 in the place where gauze pad 24 is shown in FIG. 1.

The aluminum foil envelope 52 is used to impregnate the gauze pad 24 with silicone jelly by means of a process similar to the well known Reevlee sterilization process. A quantity of silicone jelly is enclosed in aluminum envelope 52 with a piece of sterile gauze USP and subjected to an autoclave. The silicone jelly is taken up by the gauze in a phenomenon known as thermal wicking. Instead of removing the thus impregnated gauze pad 24 from aluminum envelope 52 and assembling it into dressing 10, one can take the entire envelope 52 and assemble it in to dressing 10 in the same manner as described in connection with FIG. 1. Bottom aluminum sheet 56 will be removed along with release paper 40 prior to applying the dressing to the wound.

The process of removing lower aluminum sheet 56 may be facilitated by adhesively connecting the bottom of lower sheet 56 to the confronting surface of release paper 40 so that when one removes release paper 40, one pulls lower aluminum sheet 56 with it. In a further alternative embodiment, a separation string 64 may be inserted along one or more sides of perimeter 58 of envelope 52 to assist in the removal of lower aluminum sheet 56.

It can be seen that the silicone gauze occlusive dressing of the present invention may be used to effectively treat penetrating thoracic trauma wherein the risk of open and/or tension pneumo/hemo thorax is significant. The dressing will be able to prevent the entrance of air into the thoracic cavity utilizing the occlusive dressing features of the invention while allowing for the escape of fluids such as air and blood when necessary, utilizing the flutter valve features of the invention.

Those skilled in the art will appreciate that many modifications can be made to this preferred embodiment while staying within the scope of the present invention. Thus, it is not intended to limit the scope of the invention except as set forth in the attached claims.

What is claimed is:

1. A wound dressing comprising:
   a. a generally rectangular gauze pad having a top and a bottom and having a perimeter defining in area sufficient to occlude the wound;
   b. silicone impregnated into said gauze pad;
   c. a thin, flexible, generally rectangular outer sheet having a perimeter which overlaps the pad on all four sides and having:
      i. a generally rectangular marginal area extending along one side of the generally rectangular sheet, one side of said marginal area aligned co-linearly with an adjacent portion of the pad perimeter and
      ii. an adhesive area covering at least a major portion of remainder of said sheet;
   d. at least one adhesive layer securing said sheet adhesive area to said top of said pad and overlapping three sides of said pad so that the dressing may be adhesively affixed to the patient's skin about the wound and leaving the dressing unadhered to the skin on the remaining side of the pad so that undesired fluids can escape from the wound and drain out of the dressing.

2. The wound dressing of claim 1 wherein said outer sheet is fluid impervious.

3. The wound dressing of claim 1 wherein the one side of said marginal area which is aligned co-linearly with an adjacent portion of the pad perimeter is a border line spaced inwardly from the perimeter of said outer sheet, said border line defining the difference between said adhesive area and said marginal area of said outer sheet.

4. The wound dressing of claim 1 wherein said adhesive layer covers all of the remainder of said adhesive area.

5. The wound dressing of claim 1 wherein said adhesive layer is substantially continuous.

6. The wound dressing of claim 1 further including an aluminum envelope enclosing said silicone impregnated gauze pad, said envelope including an upper sheet and a lower sheet crimped together around its perimeter.

7. The wound dressing of claim 6 further including means for attaching said upper aluminum sheet to said gauze pad.

8. The wound dressing of claim 7, wherein said attachment means includes a stitch.

9. The wound dressing of the claim 7 wherein said attaching means includes adhesive.

10. The wound dressing of claim 6 further including a separation string for separating the upper and lower sheets of said aluminum foil envelope for assisting in removal of said lower sheet prior to application of the wound dressing to the wound.

11. An occlusive wound dressing comprising:
   a. a gauze pad having a top and a bottom and having a perimeter defining in area sufficient to occlude the wound;
   b. silicone impregnated into said gauze pad;
   c. a thin, flexible outer sheet overlapping at least a substantial portion of the perimeter of said pad and having:
      i. an adhesive area defining a major portion of the area of said outer sheet; and,
      ii. a marginal, non-adhesive portion on a portion of the periphery of said outer sheets, a border of said marginal portion being at least partially co-linear with a portion of the perimeter of said gauze;
   d. adhesive material securing such outer sheet adhesive area to said top of said pad and overlapping said pad so that the dressing may be adhered to the skin of the patient and leaving the dressing unadhered to the skin on at least a portion of the perimeter of the pad so that undesired fluids can escape from the wound and drain out of the dressing.

12. The wound dressing of claim 11 wherein said gauze pad is made of cotton.

13. The wound dressing of claim 11 wherein said adhesive material is a continuous layer.

14. The wound dressing of claim 11 wherein said outer sheet is fluid impervious.

15. The wound dressing of claim 11 further including release paper covering said outer sheet and contacting said adhesive material and overlaying said gauze pad to form with said outer sheet an enclosure for said gauze pad.

16. The wound dressing of claim 11 wherein said gauze pad is rectangular.

17. The wound dressing of claim 11 further including a sterile package enclosing said dressing.

* * * * *